United States Patent [19]
Brooks et al.

[11] 4,450,833
[45] May 29, 1984

[54] METHOD OF DIMENSIONING A POLYURETHANE FOAM BANDAGE

[76] Inventors: William R. Brooks, 260 Arlington, Elmhurst, Ill. 60126; Irving C. Heinzel, 45 Brookdale La., Palatine, Ill. 60067

[21] Appl. No.: 326,933

[22] Filed: Dec. 2, 1981

[51] Int. Cl.³ .............................................. A61F 5/04
[52] U.S. Cl. ...................................................... 128/90
[58] Field of Search ....................... 128/156, 89 R, 96; 521/902, 129

[56] References Cited

U.S. PATENT DOCUMENTS

| | | | |
|---|---|---|---|
| 2,961,710 | 11/1960 | Stark | 18/48 |
| 3,048,169 | 8/1962 | Pierce | 128/90 |
| 3,373,741 | 3/1968 | Hill et al. | 128/90 |
| 4,309,990 | 1/1982 | Brooks et al. | 128/90 |
| 4,316,457 | 2/1982 | Liegeois | 128/90 |
| 4,331,134 | 5/1982 | Brooks et al. | 128/90 |

OTHER PUBLICATIONS

Tower Company Inc., *Aire Cast Suggested Aids in Perfecting An Aire-Cast*, Jan 17, 1950, p. 2.

Primary Examiner—Henry J. Recla
Assistant Examiner—Karin M. Reichle
Attorney, Agent, or Firm—John S. Fosse

[57] ABSTRACT

A cellular synthetic medical cast is made using fabric strips and a dispenser unit containing blowing agent and a water-activatable polyurethane prepolymer under superatmospheric pressure. A trimerizing catalyst is infused in the prepolymer mass immediately before the composition is dispensed in a bead onto the fabric strip; and thereafter, mechanical compressive force is applied to the foam bead to dimension it, embed it in the fabric and regulate the degree of reticulation. The impregnated strips are wrapped to form the cast and contacted with moisture to produce rapid cure of the prepolymer.

9 Claims, 6 Drawing Figures

METHOD OF DIMENSIONING A POLYURETHANE FOAM BANDAGE

FIELD OF THE INVENTION

This invention relates generally to the art which includes medical casts, braces, splints and bandages.

The invention relates more particularly to medical dressings that are made of microcellular polyurethane foam and that are intended to be cured in place on the injured body member.

BACKGROUND OF THE INVENTION

A singular difficulty with prior art foamed-in-place medical casts has resided in the heretofore comparatively uncontrollable geometry of the finished product. Not only has the exterior of the foam cast displayed an unaesthetic, lumpy appearance but the interior has presented a ridged or undulated surface to the patient's flesh, with consequent potential for inadequate support in some regions and corresponding circulation-damaging pressure in others. These undesirable characteristics have resulted from the almost total inability to control the geometry of the foam directly issuing from a conventional foam-dispensing valve.

Prior art foam bandages have, in addition, proved to be clumsy to apply and difficult to mold properly to the injured body member.

SUMMARY OF THE INVENTION

The present invention overcomes the limitations of the prior art by providing a procedure for preparing uniformly dimensioned polyurethane foam bandage strips in an incipiently curing state. These strips are then capable of being easily wound on an injured body member in an overlapping self-adherent manner to build up a monolithic cast or splint of highly uniform wall thickness and smooth surface properties. The uniquely effective procedure of the present invention relies on forceable dimensioning of an initially mechanically, rather than chemically expanded or blown foam and subsequent reliance on chemical post-expansion of the dimensioned foam to achieve optimum properties.

Accordingly, a general object of the present invention is to provide a new and improved method of making a foam medical cast.

Another broad object of the invention is to provide a method of making a microcellular foam medical cast having controlled geometry.

A further object of the invention is to provide a method of making a cellular synthetic medical cast which firmly and uniformly embraces an injured body member to cushion it against impact blows.

These and other objects and features of the invention will become more apparent from a consideration of the following descriptions.

BRIEF DESCRIPTION OF THE DRAWING

In order that the principles of the invention may be readily understood, schematic illustrations of one method of making a dimensioned polyurethane foam bandage, but to which the application is not to be restricted, are shown in the accompanying drawing wherein.

DETAILED DESCRIPTION OF THE INVENTION

Figure 1:
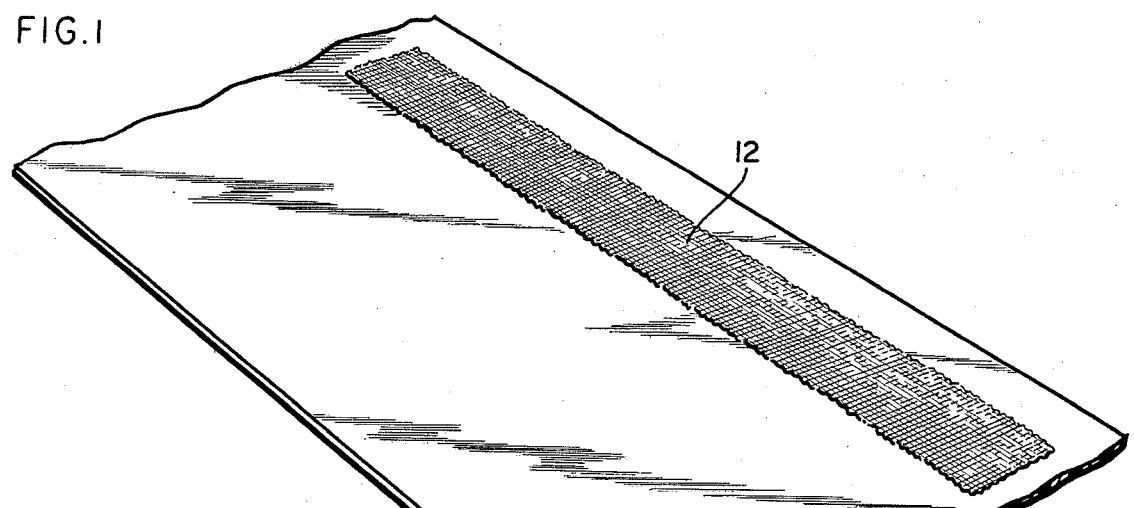
FIG. 1 is a schematic perspective view showing a fabric strip stretched out on an anti-stick blanket in preparation for making a foam bandage.

The present invention provides a process for the on-site production of a medical cast from a foamable composition that comprises a prepolymer of polymer precursor, typically an hydroxyl-poor reaction product which is curable on contact with a source of water, in admixture with a polymer-soluble, inert frothing agent. The composition is held under such superatmospheric pressure that the frothing or blowing agent exists in substantially condensed or liquid form. In addition, the composition is capable of expanding, on release of the pressure and vaporization of the blowing agent, to form a foam which then cures on contact with moisture. Preferred compositions produce microcellular foams which contain at least about 40% and preferably between about 60% and about 70% open or reticulated cells.

In compliance with an important feature of the present invention, an active trimerizing catalyst is injected into and dispersed throughout the pressurized prepolymer mass immediately prior to dispensing the foam in making a medical cast. By thus increasing the reactivity of the foam composition, the present invention achieves a fast "set time" in the resultant medical cast for rapidly immobilizing a fractured limb, for example, and correspondingly reducing the amount of physician's and technician's time necessary to complete the medical procedure.

One eminently useful group of normally liquid, trimerizing catalysts is the tertiary amines, such as dimethylbenzlamine, triethylenediamine, N,N,N',N'-tetramethyldiaminoethyl ether, bis-(dimethylaminopropyl)-urea, N-methyl and/or N-ethyl morpholine, 1,2-dimethylamidazole and dimethyl piperazine. The use of trimerizing catalysts in reacting isocyanates is also described in U.S. Pat. No. 2,993,870 which reference is made for completeness of disclosure. A minimum of 1½ parts of trimerizing catalyst per 100 parts of prepolymer by weight is required in the practice of the invention, preferably about 2.0 to about 2.9 parts per hundred. The selected tertiary amine catalyst may be used neat or mixed with a vehicle or with another catalyst such as dibutyltin dilaurate.

The prepolymer used in the process of the invention may be any water-catalyzable liquid prepolymer or polymer precursor that, at ambient temperature, has a sufficiently low viscosity to enable it to be dispensed at the desired rate but a sufficiently high viscosity to enable a stable foam or froth to be produced.

Polyurethane prepolymers are particularly suitable for use in the process of the invention since they are water-catalyzable and hence may be cured by the moisture in the atmosphere, or by a spray of atomized water droplets, or by contact with a moistened bandage or cast garment. Polyurethane prepolymers have been fully described in the prior art and the factors influencing their viscosity are well known. In general, a polyurethane prepolymer is obtained by reacting an organic polyol with a controlled amount of an organic polyisocyanate, the product having unreacted isocyanate radicals which function to cure the resinous mass upon exposure to water and which trimerize in the presence of the catalyst of the invention.

Polyurethane prepolymers for use in making medical casts in accord with the invention may be prepared from any organic polyisocyanate that is liquid at ambient temperature and any organic polyol which has molecular weight of at least about 300 and which is also liquid at ambient temperature.

Several polyisocyanates have been described in the prior art for use in polyurethane processes, such as tolyene diisocyanate which is available as the 2,4-isomer or as mixtures of the 2,4- and 2,6-isomers. Any of the available grades may be used in distilled or crude form. Also useful are the crude diphenylmethane diisocyanate compositions, particularly those containing from 30% to 90%, preferably from 40% to 80%, by weight of diphenylmethane diisocyanate, the remainder being polyisocyanates of functionality greater than two.

Organic polyols suitable for use in making the polyurethane prepolymers of the invention include reaction products of one or more alkylene oxide compounds with a hydrogen-donor compound, such as ethylene glycol, propylene glycol, glycerol, sorbitol and various amino-alcohols. These reaction products desirably have molecular weights of between 300 and 8000 according to the amount of alkylene oxide reacted with the active hydrogen-containing compound. Other suitable polyols are polyesters which may be made, for example, from polycarboxylic acids and polyhydric alcohols.

The prepolymers of the invention are prepared by reacting the organic polyisocyanate with the organic polyol in known manner. The viscosity of the prepolymer will depend upon the constitution of the starting materials and on the amount of unreacted isocyanate. In general, the use of a polyol having a high functionality and a high hydroxyl number gives high viscosity prepolymers while the use of appreciable excesses of polyisocyanate tends to reduce the viscosity.

Prepolymers for use in the invention may conveniently be made by reacting an organic polyol with from 2 to 5 mol equivalents of an organic polyisocyanate. For a rigid foam, the use of approximately 3 to 4 mol equivalents of polyisocyanate per mol of polyol has been found to be preferable.

The frothing or blowing agent used in the present invention is a material which is medically safe, which is inert towards the other ingredients of the system, and which has a sufficiently low boiling point to enable it to vaporize rapidly when the pressure is released. Suitable inert blowing agents are those that have already been proposed for use in making polyurethane foams, including halogenated hydrocarbons having boiling points not exceeding about 50° C. at atmospheric pressure and particularly fluorinated hydrocarbons. Dichlorodifluoromethane is a particularly suitable blowing agent because of its low boiling point. In situations where it is desired to use lower pressures, a mixture of dichlorodifluoromethane and trichlorofluoromethane is more suitable because of the lower volatility of such a mixture. The amount of frothing or blowing agent in the foamable compositions may be varied according to the foam density which it is desired to achieve and may range from 10% to 100% or more based on the weight of prepolymer.

The foamable compositions prepared in accordance with the invention may also contain other conventional ingredients of polyurethane foam formulations, including surfactants, such as organosilicon polymers, which serve to stabilize the foam until cure has taken place.

The foamable compositions of the present invention are converted into foamed plastics material by infusion of catalyst and releasing the pressure on the resinous mass. On reducing the pressure, the foamable composition expands rapidly to give a froth, the final volume of which is quickly attained. Because initial foaming is entirely due to the release of pressure and not to vaporization caused by the heat resulting from a chemical reaction, the initial volume of the froth tends to remain substantially unchanged after attainment of ambient pressure has taken place.

Upon contact with water, cure of the polymeric froth takes place beginning at the surface and then proceeding inwardly of the foam mass due to the diffusion of moisture into the foam; and comparatively rigid foam formulations are selected in order to provide proper mechanical support for the immobilized human body part. Such rigid foams are produced from polyols having from 3 to 8 hydroxyl groups per molecule and hydroxyl numbers of from 200 to 800, preferably 400 to 600.

The foamable compositions of the invention are prepared in bulk and then charged into containers of appropriate size, the pressure being releasable at the time of cast-making by some convenient valve arrangement. The containers may vary in size according to the volume of the cast that is to be made.

In addition to a catalyst injection device and a supply of pressurized containers filled with a water-catalyzable polyurethane prepolymer composition, the making of microcellular medical casts according to the present invention requires the availability of elongate bandage strips. While conventional surgical cotton gauze may be used, ribbed two-way stretch gauze or fabric of a synthetic fiber such as polyester is preferred to enhance conformability to the injured limb and provide a substrate to which the foam readily adheres. Provision of a suitable, wettable undergarment to wrap on the patient's limb is also highly desirable to serve as a source of moisture in contact with the inside surfaces of the cast to commence cure of the foam adjacent the body part being immobilized.

Assuming that all of the necessary supplies and components are at hand and assuming for purposes of description that a person's broken wrist is to be immobilized, preparation of a foam medical cast in accordance with present invention will now be described with reference to the drawings, commencing with FIG. 1.

To initiate making the foam bandage, a flexible antistick or release blanket 10 will first be laid out flat on a tabletop or other horizontal surface. The blanket 10 advantageously comprises either a low-cost, disposable polyethylene film of suitable guage or some other flexible sheet material to which polyurethane foam is only weakly adherent. Next, a gauze or fabric bandage strip 12 of preselected length will be stretched out on the blanket 10 to receive a bead of foam. Bandage strips three or four inches wide and 30 to 40 inches long have proved convenient to manipulate; and a suitable quantity of bandage strip may be provided in a storage roll dispenser carton.

Figure 2:
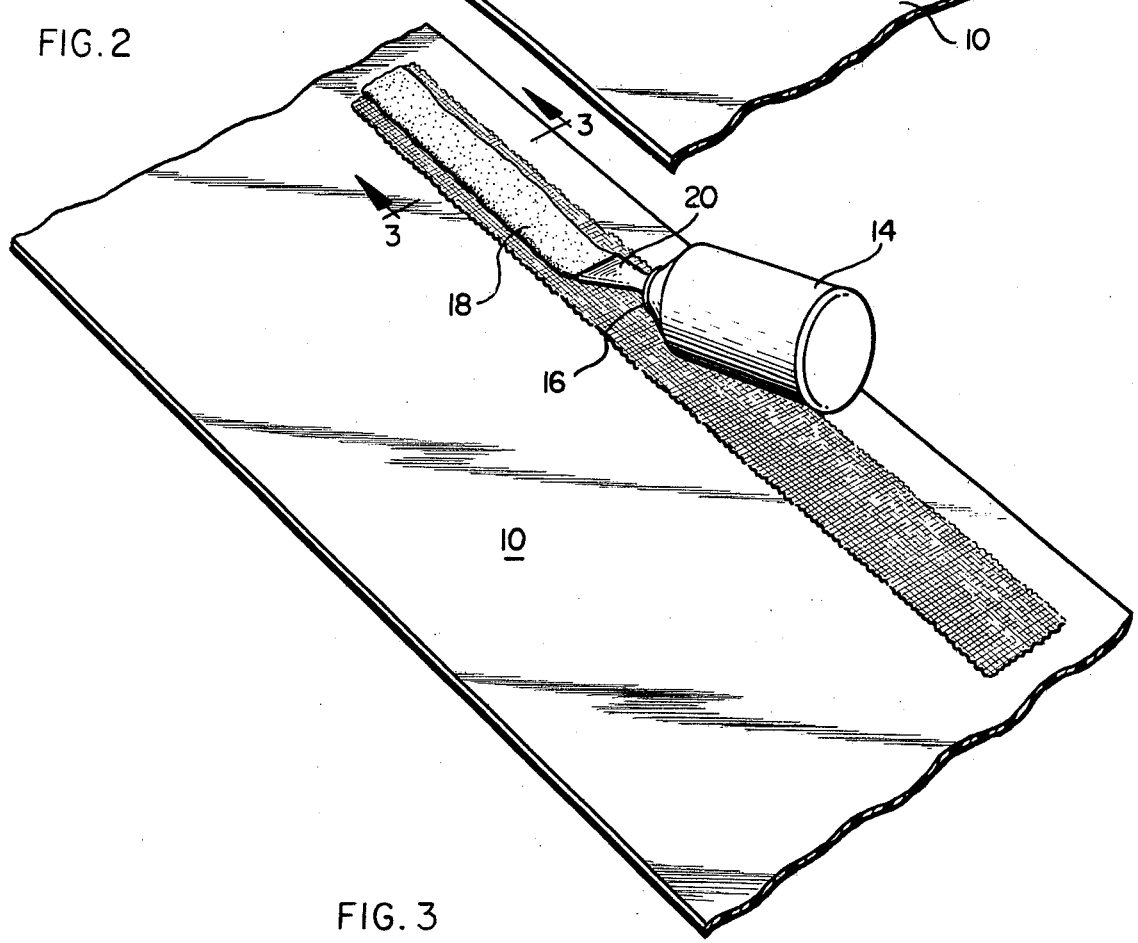
FIG. 2 is a view similar to the showing of FIG. 1 but additionally illustrating the dispensing of an incipiently reacting polyurethane foam bead from a pressurized dispenser onto the bandage strip.
Figure 3:
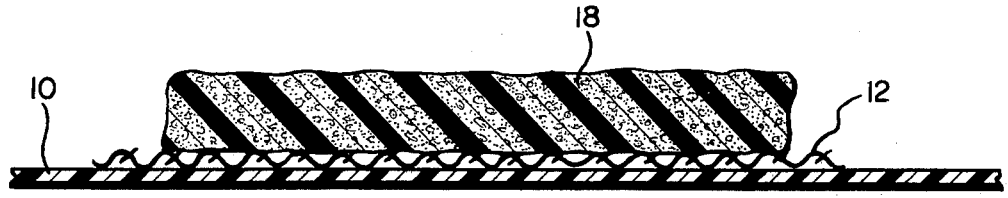
FIG. 3 is an enlarged sectional view taken substantially along the line 3—3 of FIG. 2 to show the irregularities in the dimensions of the dispensed foam bead.
Figure 4:
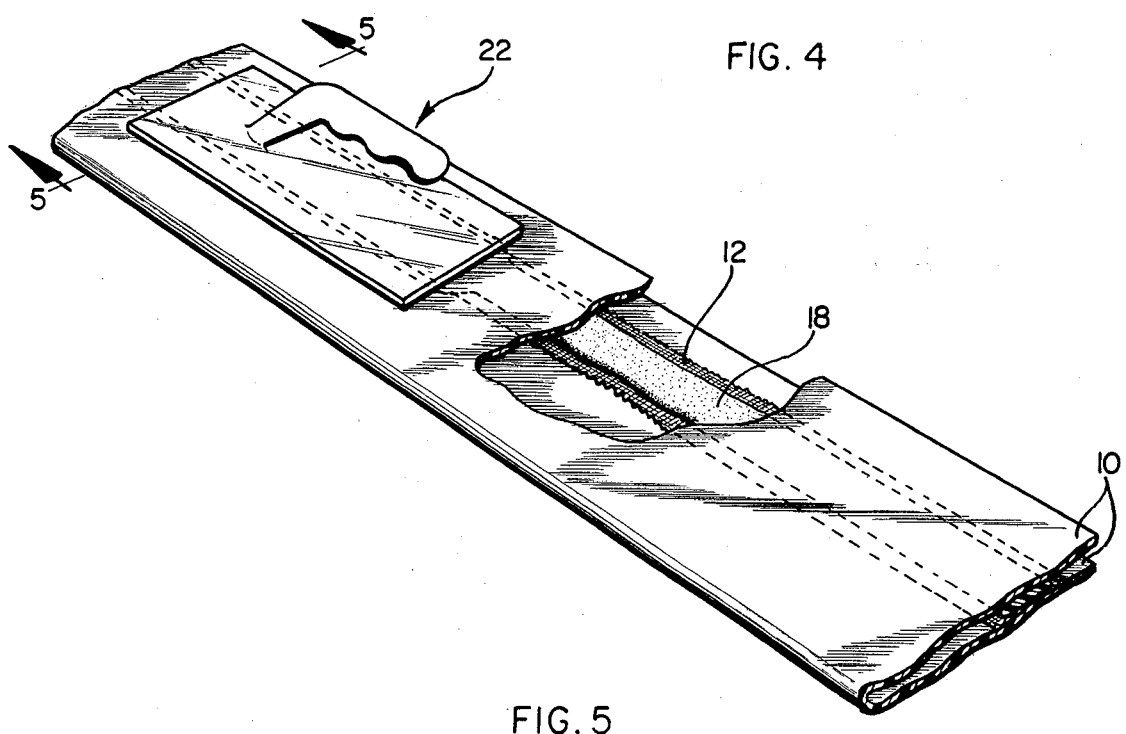
FIG. 4 is a view similar to the showing of FIG. 2 but illustrating the anti-stick blanket having been folded over on top of the gauze strip after completion of the foam bead and further illustrating use of a trowel in mechanically tamping the foam bead to a uniform thickness.

With the selected length of bandage strip laid out on the anti-stick blanket 10, a pressurized dispenser-container 14 that has been filled with a suitable quantity of polyurethane prepolymer composition will be activated by injecting a metered amount of a liquid trimerizing catalyst through a conventional valve mechanism 16 mounted on the cannister 14, or through a grommet fixed in the container wall. The container will be shaken by hand to mix the catalyst throughout the prepolymer system; and then a bead 18 of foam or froth will be manually dispensed from the container advantageously utilizing a conventional fan nozzle 20 connected to the valve mechanism 16, as is illustrated in FIG. 2. Continuing with reference to FIG. 3, the ambiently dispensed bead 18 will be of somewhat irregular height and width and may extend over the edges of the bandage strip 12 or be spaced inboard from the edges thereof.

Figure 5:
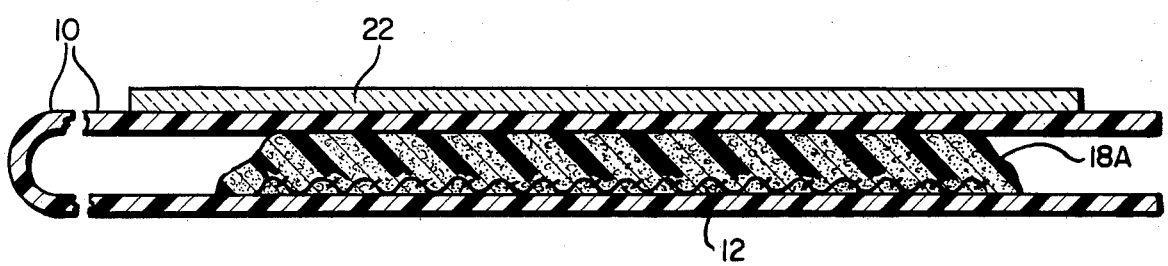
FIG. 5 is an enlarged sectional view taken substantially along the line 5—5 of FIG. 4 to show dimensioning of the foam bead.

In compliance with the present invention, and in order to establish uniform height or thickness and uniform width in the foam bead, and in order to regulate the degree of openness of foam cells, the anti-stick blanket 10 will next be folded over the foam impregnated bandage strip, as is suggested in FIG. 5; and thereafter, mechanical compressive or tamping force will be applied to the top layer of the blanket of release material, manually mashing the dispensed foam against the rigidity of the underlying tabletop, conveniently utilizing a transparent plastic trowel 22. This compressing, mashing or squeezing of the foam bead will proceed in steps along the entire length of the impregnated strip in order to produce a bead 18A of uniform height and having a controlled degree of open cell structure. It is to be recognized that a rolling force applied to the dispensed foam bead tends to extrude and distort the geometry of the foam and is therefore undesirable. It is also important to recognize that the chemistry of polyurethane prepolymers requires a mechanical blowing or frothing in order to make foam initially; and the present application of a tamping-type compressive force to the dispensed foam bead increases the foam density and its degree of cell reticulation, as well as increases the rigidity of the cured foam, thus enhancing mechanical support of the fracture or other injury to be immobilized. Provision of the instant trimerizing catalyst is necessary to restore the optimum physical properties of the foam after mechanical dimensioning and cell conditioning.

Figure 6:
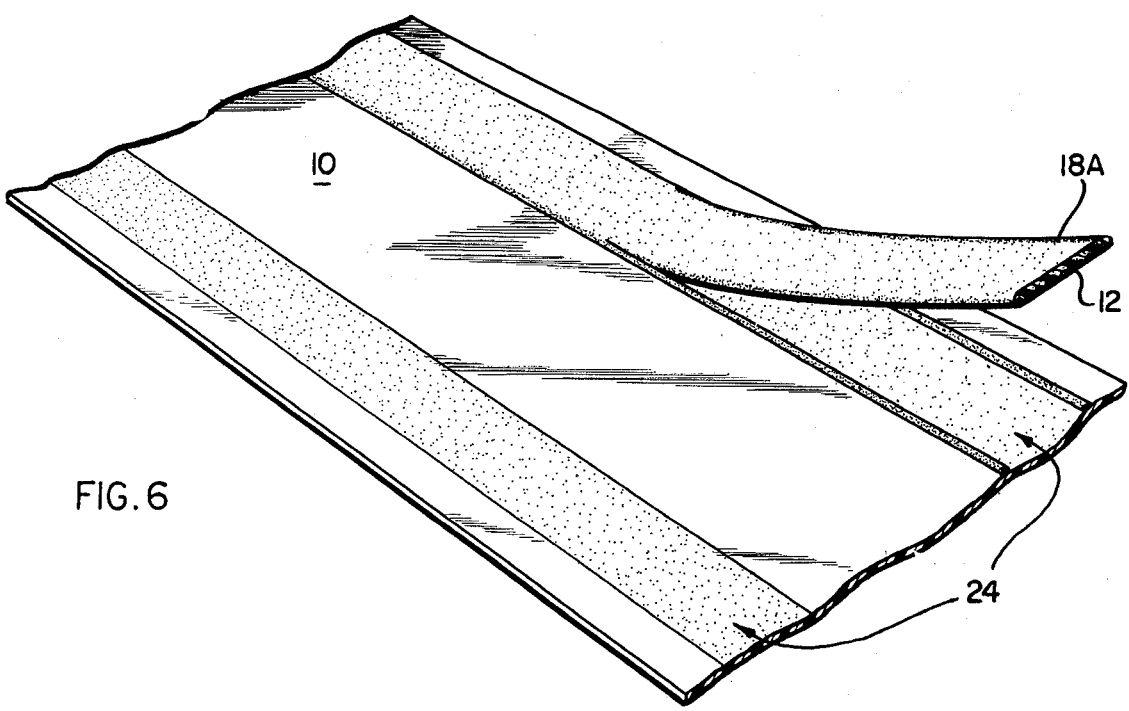
FIG. 6 illustrates lifting of the foam impregnated bandage strip from the anti-stick blanket after the same has been unfolded and suggesting quanta of the foam residue left on the blanket.

A suitable undergarment will next be moistened with water and then placed on the patient's injured limb, whereupon the anti-stick blanket 10 will be folded back and the foam impregnated bandage strip lifted from the blanket as suggested in FIG. 6. Since the bead of foam 18A has been catalyzed but no moisture added, keeping the blanket folded over the flattened foam bead prevents invasion by atmospheric moisture and thus slows cure until the impregnated bandage strip is removed and placed in contact with the moisture of the moistened undergarment. Immediately upon contact with water, the foam will commence to cure; and while subsequent strips of impregnated bandage are prepared and wrapped to form the completed cast, the foam may be molded to conform to the limb and fix the fracture. Advantageously, a moistened overgarment or a water spray will be applied when wrapping is completed in order to expose the exterior of the cast to catalytic moisture and in order to prevent adherence of the tacky foam to the operator's hands for example. Exposure to moisture reacts the catalyzed prepolymer, restoring optimum physical properties after uniform geometry has been mechanically achieved.

It will be noted with reference to FIG. 6, that residual quantities 24 of the foam, particularly those quantities situated beyond the sides of the gauze strip 12, are deposited on the blanket 10. Stripping of the impregnated bandage strip from the blanket thus controls the width dimension of the impregnated strip by leaving behind these quantities of foam lateral of the bandage strip.

The initial frothing of the foam composition takes place immediately upon release from the dispenser 14; and by selection of the prepolymer formulation and the amount of catalyst that is injected, a "green set" may be achieved in the finished medical cast in approximately six to eight minutes. Complete cure of the foam will be accomplished in about four to five hours.

An appearance of cleanliness sleeve may be slipped over the finished cast as an overwrap if desired.

The resultant foam bandage or cast is sufficiently rigid to immobilize the patient's injured limb, yet sufficiently resilient to cushion the limb and protect it from accidental blows. The foam cast of the invention is also extremely lightweight, transparent to X-rays, undamaged by immersion in water, and produces no harmful or noxious break-down products. It is made self-extinguishing as regards flammability but may be disposed of by incineration and does not itself support bacterial growth.

The specific embodiment herein described is to be considered primarily illustrative. Various changes beyond those described will, no doubt, occur to those skilled in the art; and such changes are to be understood as forming a part of this invention insofar as they fall within the spirit and scope of the appended claims.

The invention is claimed as follows:

1. The method of making a cellular synthetic bandage member which comprises the steps of: providing a dispenser package which includes a water-activatable prepolymer composition under superatmospheric pressure and a blowing agent for said composition; storing said package; thereafter infusing a trimerizing catalyst throughout said packaged composition in continuation of said superatmospheric pressure and at substantially the time of use; dispensing an elongate quantity of said composition into contact with a fabric element at ambient pressure whereby to activate said blowing agent in causing said composition to form flexible froth foam adhering to said fabric element; applying mechanical compressive force to said froth foam to squeeze said foam into intimate contact with said fabric element, reduce the thickness dimension of said foam, and embed said fabric element in said foam; and contacting the surfaces of the resultant foam bandage member with moisture while making a medical dressing, whereby to cause said moisture to react said prepolymer composition in the presence of said trimerizing catalyst, partially restoring the pre-compressed thickness of said foam and its cellular structure and curing the foam to a level of optimum properties.

2. The method of making a cellular synthetic bandage member according to claim 1 wherein said prepolymer composition is a polyurethane prepolymer composition and wherein said trimerizing catalyst includes a tertiary amine.

3. The method of making a cellular synthetic bandage member according to claim 2 wherein said blowing agent comprises dichlorodifluoromethane.

4. The method of making a cellular synthetic bandage member according to claim 1 which comprises sandwiching said froth foam and fabric element between layers of an anti-stick material during application of the mechanical compressive force.

5. The method of making a cellular synthetic bandage member according to claim 1 wherein said fabric element is a ribbed stretch fabric of synthetic fiber.

6. The method of making a cellular synthetic bandage member which comprises the steps of: providing a dispenser package which includes a water-activatable prepolymer composition under superatmospheric pressure and a blowing agent for said composition; infusing a trimerizing catalyst through said composition in continuation of said superatmospheric pressure at substantially the time of use; dispensing an elongate quantity of said composition into contact with a fabric element at ambient pressure whereby to activate said blowing agent in causing said composition to form flexible froth foam adhering to said fabric element; and contacting the surface of the resultant foam bandage member with moisture while making a medical dressing, whereby to cause said moisture to react said prepolymer composition in the presence of said trimerizing catalyst and cure the foam to a level of optimum properties.

7. The method of making a cellular synthetic bandage member according to claim 6 wherein said prepolymer composition is a polyurethane prepolymer composition and wherein said trimerizing catalyst includes a tertiary amine.

8. The method of making a cellular synthetic bandage member according to claim 7 wherein said blowing agent comprises dichlorodifluoromethane.

9. The method of making a cellular synthetic bandage member which comprises the steps of: providing a dispenser package which contains a water-activatable prepolymer composition under superatmospheric pressure and a blowing agent for said composition; storing said package; thereafter infusing a trimerizing catalyst throughout said composition in continuation of said superatmospheric pressure and at substantially the time of use; dispensing an elongate quantity of said composition into contact with a fabric element at ambient pressure whereby to activate said blowing agent in causing said composition to form flexible froth foam adhering to said fabric element; contacting the surfaces of the resulting foam bandage member with moisture while making a medical dressing; and applying mechanical compressive force to the froth foam before said moisture fully reacts said prepolymer composition in the presence of said trimerizing catalyst, said compressive force serving to dimension said froth foam and reticulating a portion of its cells, said moisture and catalyst cooperating to partially restore the initial dimension of the foam and curing it to a level of optimum properties.

* * * * *